(12) United States Patent
Milliman et al.

(10) Patent No.: US 8,403,942 B2
(45) Date of Patent: Mar. 26, 2013

(54) ANVIL DELIVERY DEVICE ACCESSORY

(75) Inventors: Keith L. Milliman, Bethel, CT (US);
Thomas Wenchell, Durham, CT (US);
Philip C. Roy, Orange, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/358,304

(22) Filed: Jan. 25, 2012

(65) Prior Publication Data

US 2012/0123457 A1   May 17, 2012

Related U.S. Application Data (62) Division of application No. 12/207,562, filed on Sep. 10, 2008.

(60) Provisional application No. 60/995,023, filed on Sep. 24, 2007.

(51) Int. Cl.
*A61B 17/11* (2006.01)
*A61B 17/115* (2006.01)

(52) U.S. Cl. ............... 606/108; 606/153; 227/175.1

(58) Field of Classification Search ............ 606/108, 606/153, 190, 191; 128/898; 227/175.1–182.1
See application file for complete search history.

(56) References Cited

U.S. PATENT DOCUMENTS

| | | | |
|---|---|---|---|
| 4,195,624 A | 4/1980 | Douglas | |
| 4,263,914 A | 4/1981 | Pawlak | |
| 4,304,236 A | 12/1981 | Conta et al. | |
| 4,319,576 A | 3/1982 | Rothfuss | |
| 4,328,805 A | 5/1982 | Akopov et al. | |
| 4,379,457 A | 4/1983 | Gravener et al. | |
| 4,473,077 A | 9/1984 | Noiles et al. | |
| 4,476,863 A | 10/1984 | Kanshin et al. | |
| 4,537,193 A | 8/1985 | Tanner | |
| 4,573,468 A | 3/1986 | Conta et al. | |
| 4,576,167 A | 3/1986 | Noiles | |
| 4,603,693 A | 8/1986 | Conta et al. | |
| 4,646,745 A | 3/1987 | Noiles | |
| 4,667,673 A | 5/1987 | Li | |
| 4,712,536 A | 12/1987 | Hawks | |
| 4,773,417 A * | 9/1988 | Moore et al. | 606/80 |
| 4,817,847 A | 4/1989 | Redtenbacher et al. | |
| 4,873,977 A | 10/1989 | Avant et al. | |
| 4,976,684 A * | 12/1990 | Broadnax, Jr. | 604/540 |
| 5,005,749 A | 4/1991 | Aranyi | |

(Continued)

FOREIGN PATENT DOCUMENTS

| | | |
|---|---|---|
| EP | 1 790 295 A | 5/2007 |
| WO | WO 87/06448 A | 11/1987 |

(Continued)

OTHER PUBLICATIONS

European Search Report dated Mar. 9, 2009 in corresponding EP Appln. No. EP08253104.7 filed Sep. 23, 2008.

*Primary Examiner* — Julian Woo
*Assistant Examiner* — Christopher L Templeton (57) ABSTRACT

A method for performing a surgical procedure is disclosed which uses an anvil delivery system including an anvil assembly, a flexible tube having a first end portion and a second end portion, and a fitting to deliver the anvil assembly to a desired site. The method includes the steps of cutting a second end portion of the flexible tube, attaching a fitting to the second end portion of the flexible tube which has been cut, inserting the insertion tip into tissue, advancing the insertion tip along with the flexible tube and anvil assembly to the desired site within a patient's body, and removing the flexible tube from the anvil assembly and from the desired site leaving the anvil assembly in a patient's body at the desired site.

15 Claims, 9 Drawing Sheets

U.S. PATENT DOCUMENTS

| | | | |
|---|---|---|---|
| 5,047,039 A | 9/1991 | Avant et al. | |
| 5,104,025 A | 4/1992 | Main et al. | |
| 5,108,420 A | 4/1992 | Marks | |
| 5,119,983 A | 6/1992 | Green et al. | |
| 5,234,438 A * | 8/1993 | Semrad | 606/108 |
| 5,275,622 A | 1/1994 | Lazarus et al. | |
| 5,314,435 A | 5/1994 | Green et al. | |
| 5,531,785 A | 7/1996 | Love et al. | |
| 5,588,579 A | 12/1996 | Schnut et al. | |
| 5,766,187 A * | 6/1998 | Sugarbaker | 606/148 |
| 5,851,195 A | 12/1998 | Gill | |
| 5,893,865 A | 4/1999 | Swindle et al. | |
| 6,053,390 A | 4/2000 | Green et al. | |
| 6,149,660 A | 11/2000 | Laufer et al. | |
| 6,673,088 B1 | 1/2004 | Vargas et al. | |
| 6,918,871 B2 | 7/2005 | Schulze | |
| 7,004,175 B2 | 2/2006 | LaFontaine et al. | |
| 7,144,405 B2 | 12/2006 | Vargas et al. | |
| 7,168,604 B2 | 1/2007 | Milliman et al. | |
| 7,179,267 B2 | 2/2007 | Nolan et al. | |
| 7,628,795 B2 * | 12/2009 | Karwoski et al. | 606/108 |
| 2003/0181938 A1 * | 9/2003 | Roth et al. | 606/191 |
| 2004/0087977 A1 * | 5/2004 | Nolan et al. | 606/142 |
| 2005/0277962 A1 * | 12/2005 | Myers | 606/153 |
| 2006/0229643 A1 | 10/2006 | Nolan et al. | |
| 2007/0088389 A1 * | 4/2007 | Dunkin et al. | 606/219 |
| 2007/0106217 A1 | 5/2007 | Delegge et al. | |
| 2009/0250502 A1 | 10/2009 | Milliman | |
| 2009/0299377 A1 * | 12/2009 | Bright | 606/108 |

FOREIGN PATENT DOCUMENTS

| | | |
|---|---|---|
| WO | WO 01/66020 A2 | 9/2001 |
| WO | WO 03/030745 A | 4/2003 |

* cited by examiner

ANVIL DELIVERY DEVICE ACCESSORY

CROSS-REFERENCE TO RELATED APPLICATION

This application is a divisional application of U.S. application Ser. No. 12/207,562, filed Sep. 10, 2008, which claims priority to, and the benefit of, U.S. Provisional Patent Application No. 60/995,023, filed on Sep. 24, 2007, the entire contents of each of which are hereby incorporated by reference.

BACKGROUND

1. Technical Field

The present disclosure relates generally to a surgical apparatus for use during anastomosis procedures. More particularly, the present disclosure relates to methods and apparatus to deliver an anvil assembly to a surgical site.

2. Description of the Related Art

Surgical anastomosis is the surgical connection of severed or separate of hollow organs. Typically, an anastomosis procedure follows another surgical procedure where a diseased or defective section of hollow tissue is removed and the remaining end sections are joined. The end sections may be joined by circular, end-to-end, or side-to-side organ reconstruction methods.

In a circular anastomosis procedure, the two ends of the organ sections are joined by means of a stapling instrument that drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,168,604; 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with an attached anvil head is mounted to the distal end of the instrument adjacent the staple holding component. Opposing end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Certain circular anastomosis procedures entail minimally invasive techniques. In these procedures, surgeons often position an anvil assembly in the desired hollow organ by inserting an anvil delivery system through a patient's esophagus. U.S. Pat. No. 7,179,267, for example, describes a method and apparatus for delivering an anvil assembly through a patient's esophagus. Although surgical apparatus that can deliver an anvil assembly into a hollow organ are well-known in the art, there is a need for more versatile anvil delivery systems.

SUMMARY

The present disclosure relates to an anvil delivery system including an anvil assembly, a flexible tube, and a fitting coupled to the flexible tube. The fitting includes a body having a proximal end portion and a distal end portion, and a tip on the distal end portion. The proximal end portion is adapted to attach the body of the fitting to the flexible tube. The tip is configured for insertion into a body lumen.

The present disclosure also relates to an anvil delivery system comprising an anvil assembly, a flexible tube having a first end portion and a second end portion, and a fitting. The fitting has a proximal end portion and a distal end portion, wherein the proximal end portion is removably coupled to the second portion of the flexible tube and the distal end portion includes a tip for advancing through tissue.

In one embodiment, anvil delivery system further includes a bore extending through the distal end portion of the fitting to receive a suture. In one embodiment the anvil delivery system includes a plurality of protrusions disposed on a proximal end portion of the body of the fitting. In one embodiment, the anvil is pivotable with respect to the flexible tube.

The present disclosure also relates to a kit. The kit includes a flexible tube having a distal end an open proximal end, an adapter configured to be releasably secured to the flexible tube, and a fitting configured to be attached to the flexible tube after the distal end of the flexible tube has been cut. The fitting includes a body having a proximal end portion configured to attach to the flexible tube and a distal end portion.

In one embodiment, the kit also includes the anvil assembly.

In one embodiment, the proximal end portion of the body of the fitting is dimensioned to be supported within the flexible tube.

In one embodiment, the tip is blunt and configured for insertion into a body lumen. In one embodiment, the fitting includes a bore extending through the distal end portion of the body. In one embodiment, the plurality of protrusions is adapted to operatively attach the body of the fitting to the flexible tube.

The present disclosure also relates to method of performing a surgical procedure comprising:
  providing an anvil assembly having an anvil head and a flexible tube having a first end portion extending from the anvil assembly;
  cutting a second end portion of the flexible tube, the second end portion being disposed on an opposite end of the flexible tube from the first end portion;
  attaching a fitting to the second end portion of the flexible tube, the fitting having an insertion tip;
  inserting the second end portion of the flexible tube into a body;
  positioning the anvil assembly within the body using the flexible tube; and
  detaching the flexible tube from the anvil assembly while the anvil assembly is positioned within the body.

The fitting may include a bore to receive a suture and the inserting step may include the step of grasping the suture to pull the insertion tip to advance the fitting, flexible tube and anvil assembly. The step of attaching the fitting may include the step of inserting a portion of the fitting within the second end portion of the flexible tube to frictionally engage the tube.

BRIEF DESCRIPTION OF THE DRAWINGS

Various embodiments of the presently disclosed surgical apparatus are disclosed herein with reference to the drawings, wherein.

DETAILED DESCRIPTION OF THE EMBODIMENTS

Embodiments of the presently disclosed anvil delivery system will now be described in detail with reference to the drawings wherein like reference numerals designate identical or corresponding elements in each of the several views. In the description that follows, the term "proximal," as is traditional, will refer to the end of anvil delivery system, or a portion thereof, that is closer to the operator, while the term "distal" will refer to the end of the anvil delivery system that is farther from the operator.

Figure 1:
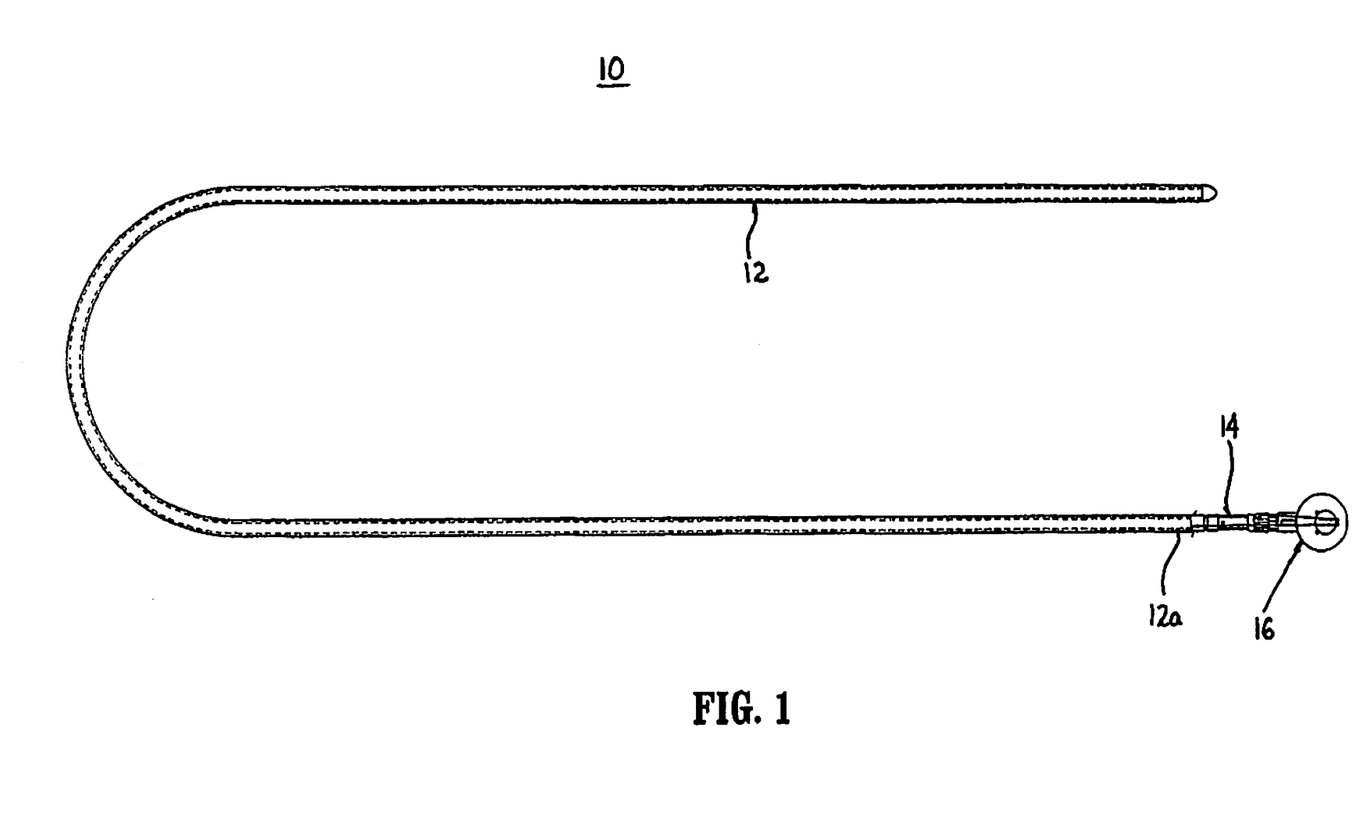
FIG. 1 is a top plan view of an anvil delivery system according to an embodiment of the present disclosure.

With reference to FIG. 1, an anvil delivery system is generally shown as 10. Anvil delivery system 10 includes a flexible tube 12, an adapter 14, and an anvil assembly 16. Anvil assembly 16 may be a 21 mm or a 25 mm anvil assembly, sold under the trademark EEA ORVIL™. Alternatively, other anvil assemblies may be used with the presently disclosed anvil delivery system. Flexible tube 12 has an open end 12a and a blunt end on the opposite end. Adapter 14 and anvil assembly 16 are supported on open end 12a of flexible tube 12, as described in detail below.

Figure 2:
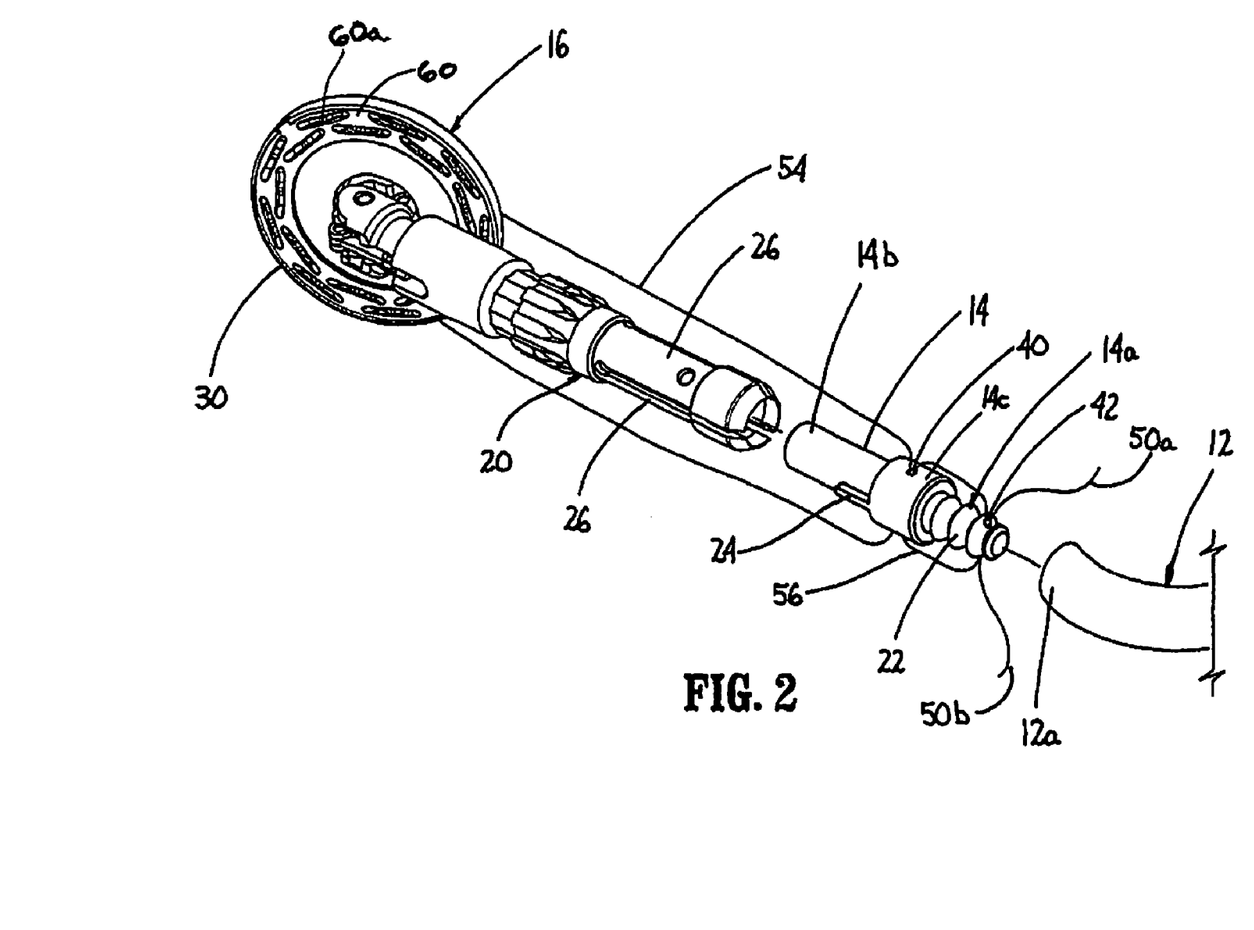
FIG. 2 is a perspective view of a portion of the anvil delivery system shown in FIG. 1.
Figure 3:
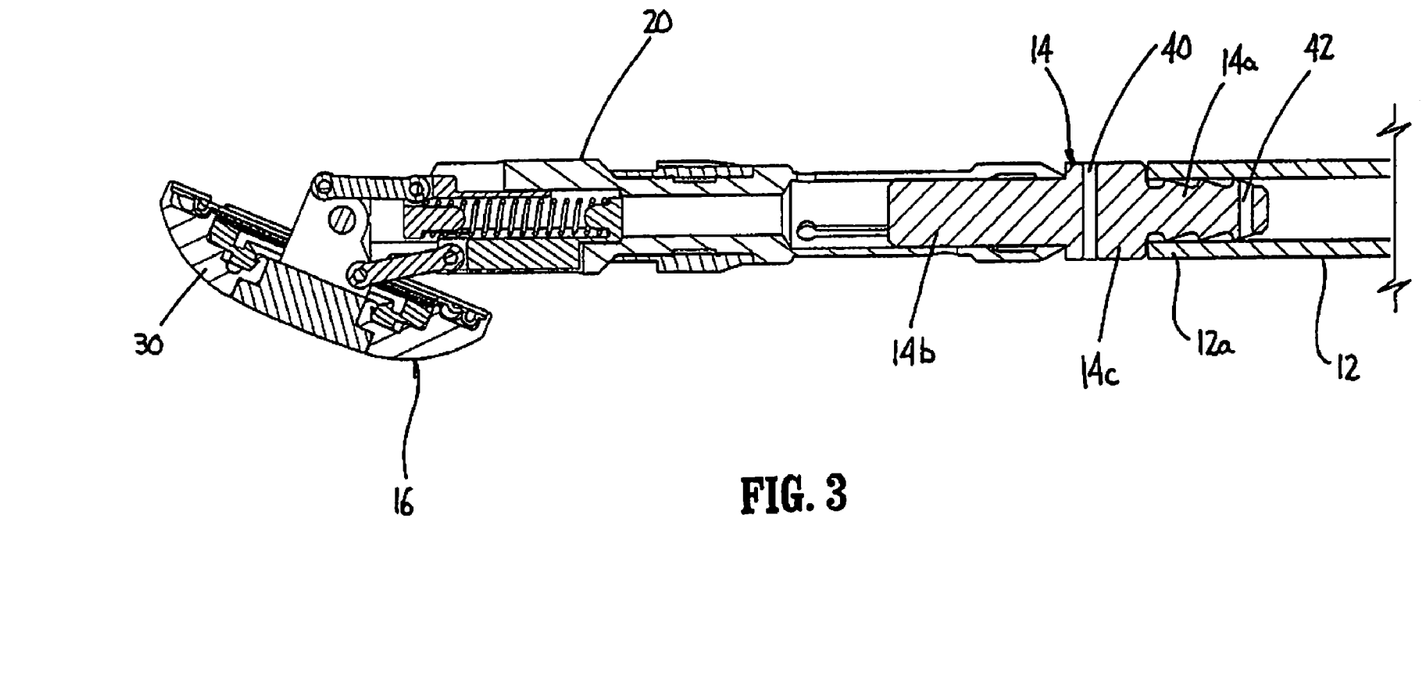
FIG. 3 is a side cross-sectional view of a portion of the anvil-delivery system shown in FIG. 1.

Referring to FIGS. 2 and 3, anvil assembly 16 includes an anvil head 30, an anvil center rod 20, and an anvil 60. Anvil 60, which is supported on anvil head 30, has a plurality of pockets 60a for receiving and deforming surgical staples. Center rod 20 is operatively connected to anvil head 30. In the embodiment shown in FIG. 2, center rod 20 is pivotably coupled to anvil head 30. Further, center rod 20 includes flexible legs 26 configured to capture at least a portion of adapter 14 therebetween.

With continued reference to FIGS. 2 and 3, adapter 14 includes a first end 14a dimensioned to be received within open end 12a of flexible tube 12 and a second end 14b configured to be received in the center rod 20 of anvil assembly 16. First end 14a includes a series of annular rings 22 dimensioned to frictionally retain first end 14a of adapter 14 within open end 12a of flexible tube 12. It is envisioned that other retaining structure can be provided to retain first end 14b of adapter 14 to flexible tube 12, e.g., clamps, pins, threads, etc. Second end 14b of adapter 14 includes a longitudinal guide member 24 dimensioned to be received between flexible legs 26 of center rod 20 of anvil assembly 16. In addition, second end 14b of adapter 14 is dimensioned to allow center rod 20 of anvil assembly 16 to freely slide on and off second end 14b of adapter 14.

Figure 4:
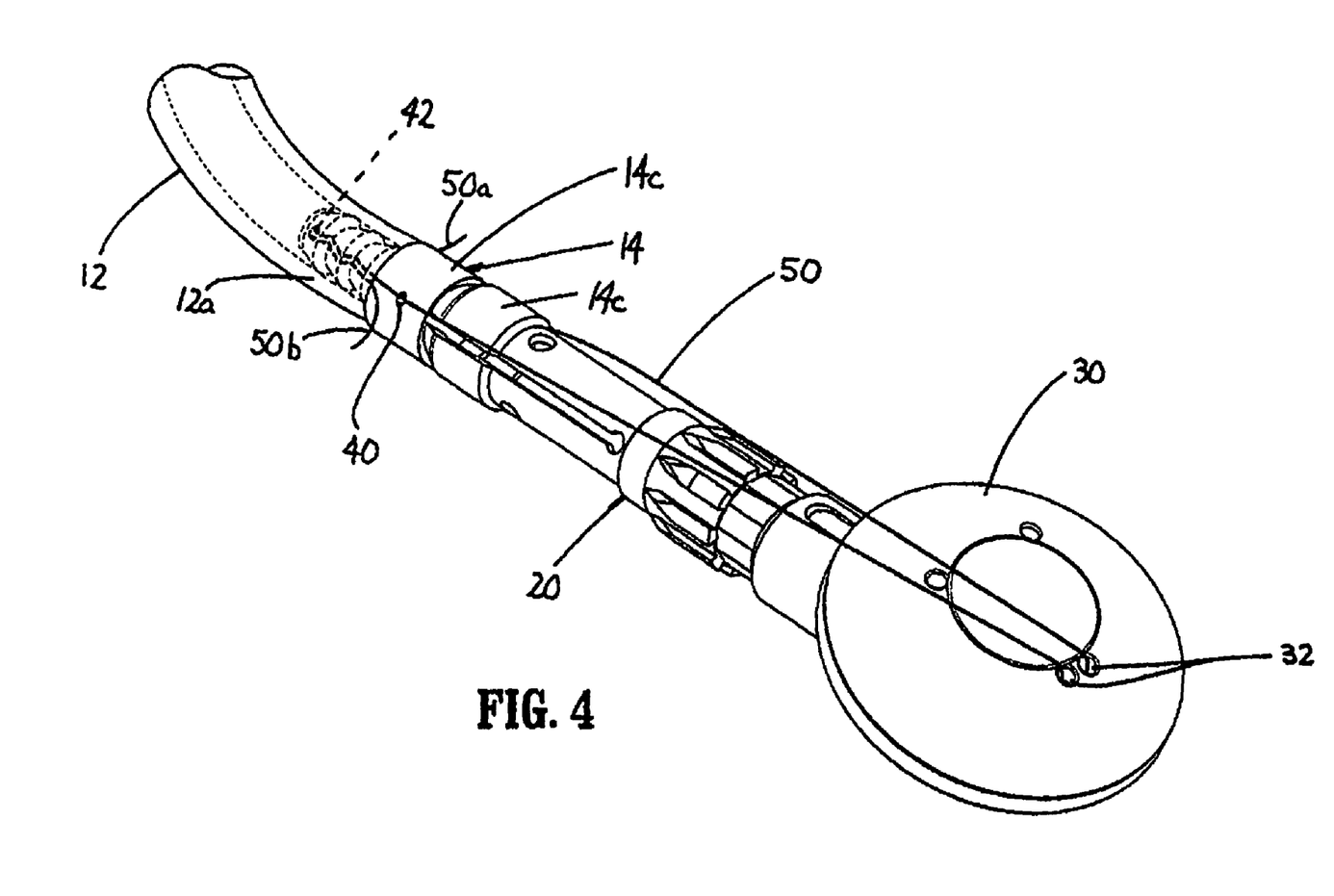
FIG. 4 is perspective view of a portion of the anvil delivery system shown in FIG. 1.
Figure 5:
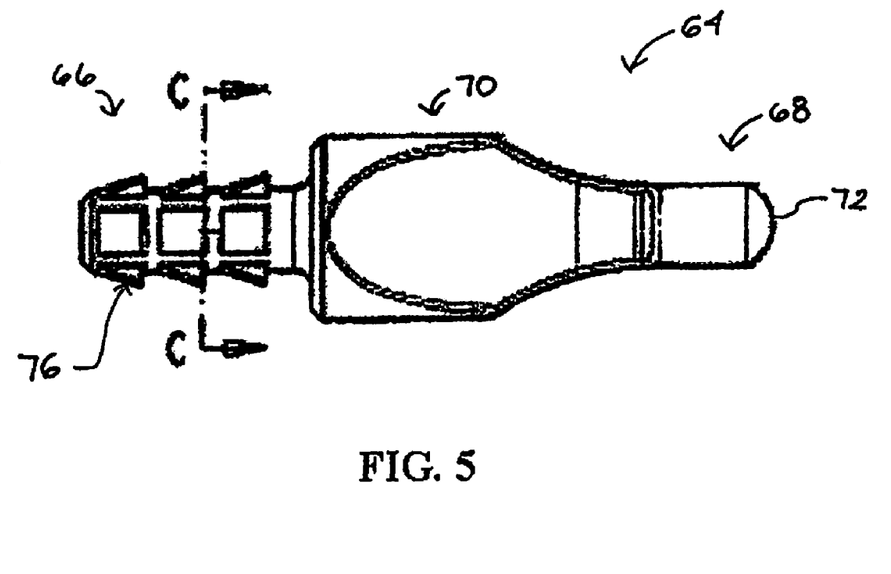
FIG. 5 is a side plan view of a fitting according to an embodiment of the present disclosure.
Figure 6:
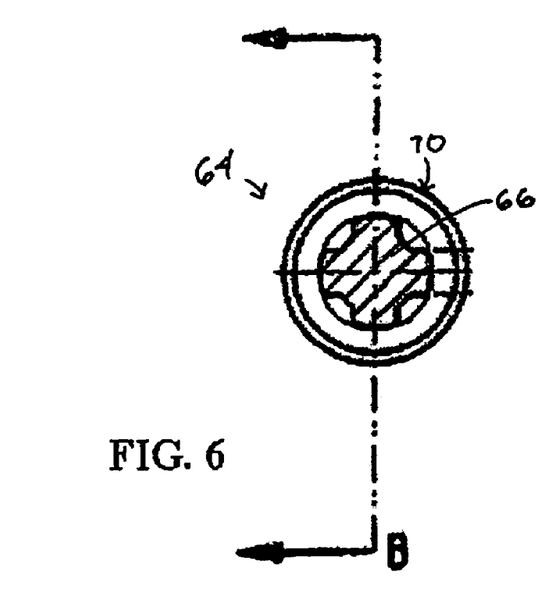
FIG. 6 is a cross-sectional rear view of the fitting shown in FIG. 5, taken along section line C-C of FIG. 5.
Figure 7:
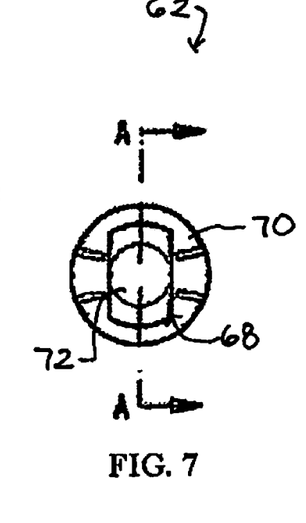
FIG. 7 is a front plan view of the fitting shown in FIG. 5.
Figure 8:
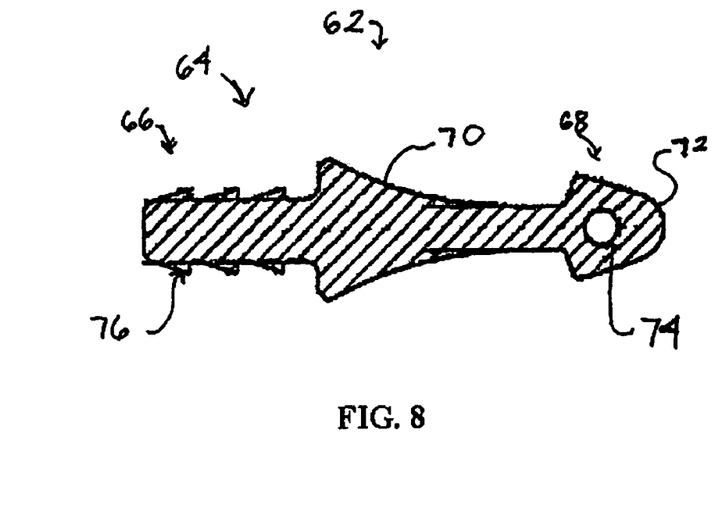
FIG. 8 is a cross-sectional side view of the fitting shown in FIG. 5, taken along section line A-A of FIG. 7.
Figure 9:
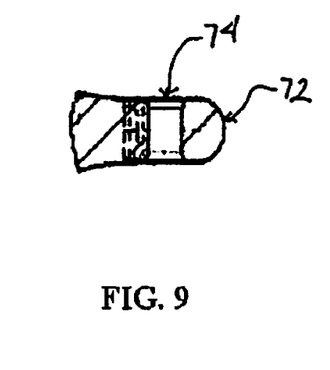
FIG. 9 is a cross-sectional side view of a portion of the fitting shown in FIG. 5, taken along section line B-B of FIG. 6.

Referring to FIG. 4, anvil head 30 of anvil assembly 16 includes spaced apart openings 32 that are in communication with each other. Adapter 14 includes a first throughbore 40 formed in a central hub portion 14c and a second throughbore 42 formed in first end 14a. As will be discussed below, anvil delivery system 10 includes a suture 50 to secure anvil assembly 16 to adapter 14.

Referring to FIGS. 2 and 4, suture 50 has a first end 50a and a second end 50b. To secure adapter 14 to anvil assembly 16, first end 50a of suture 50 is inserted into one opening 32 of anvil head 30 and pulled out of the other opening 32 such that the ends 50a and 50b of suture 50 are positioned on opposite sides of center rod 20 of anvil assembly 16. Next, second end 14b of adapter 14 is positioned within center rod 20 and each end 50a and 50b of suture 50 is inserted through an opposite end of throughbore 40 of central hub portion 14c of adapter 14 to define a first suture loop 54 (see FIG. 2). Each end 50a and 50b of suture 50 is pulled tight such that adapter 14 is held against center rod 20. Thereafter, each end 50a and 50b is inserted through an opposite end of throughbore 42 of first end 14a of adapter 14 to define a second suture loop 56 (see FIG. 2). Second suture loop 56 extends about first end 14a of adapter 14. The frictional contact between rings 22 of first end 14a of adapter 14 and the inner surface of flexible tube 12 secures adapter 14 to flexible tube 12 and prevents suture 50 from loosening up.

Figure 1A:
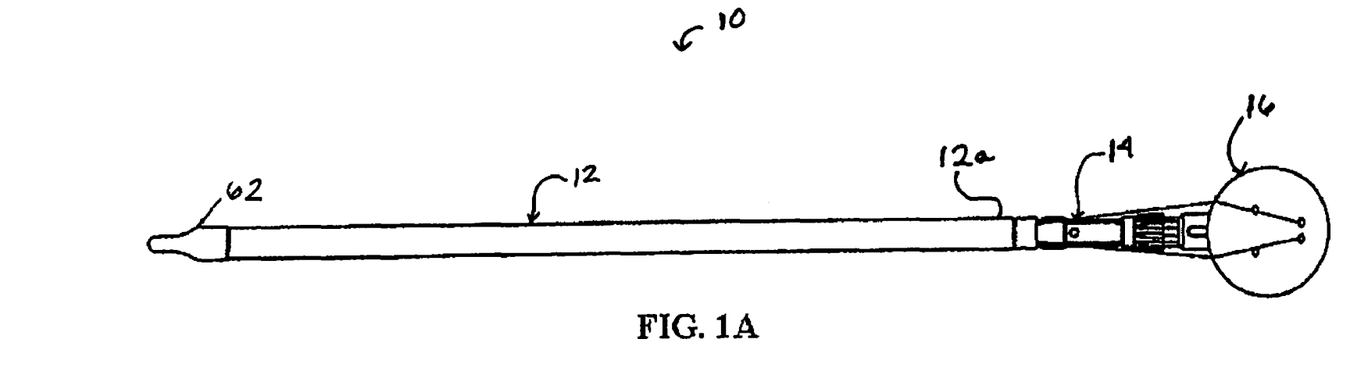
FIG. 1A is a top plan view of an anvil delivery system with a fitting attached thereto according to an embodiment of the present disclosure.
Figure 1B:
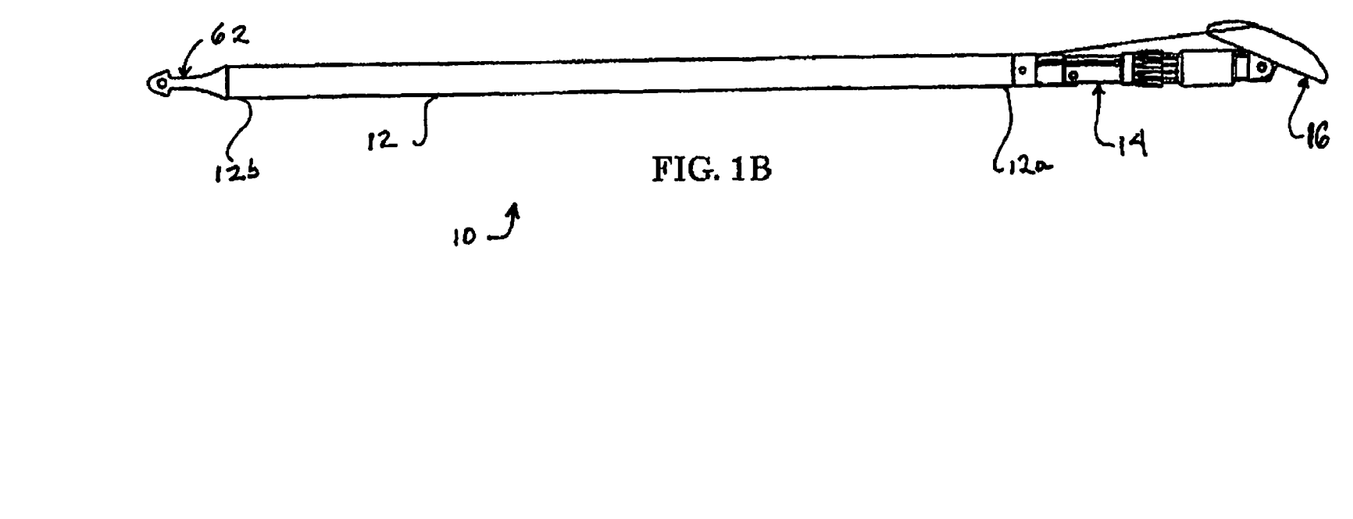
FIG. 1B is a side plan view of the anvil delivery system with the fitting shown in FIG. 1A.

With reference to FIGS. 1A and 1B, after operatively connecting flexible tube 12 to anvil assembly 16 via adapter 14, a healthcare professional may decide to shorten flexible tube 12. In some bariatric surgeries, for instance, short flexible tubes 12 are beneficial. Therefore, the healthcare professional may decide to cut flexible tube 12, thereby creating another open end 12b on the new distal end of flexible tube 12. Because the cut end of flexible tube 12 may be abrasive and/or include jagged or irregular surfaces, a fitting 62 may be attached to open end 12b of tube 12 to facilitate smooth atraumatic passage of tube 12 through or into a body lumen.

With reference to FIGS. 5-9, fitting 62 includes a body 64 having a proximal end portion 66 adapted to be supported in open end 12b of flexible tube 12, a distal end portion 68, and a middle portion 70. Distal end portion 68 has bore 74 defined therethrough and a blunt tip 72 configured for insertion into a body lumen such as the esophagus. In a preferred embodiment, the tip 72 is bullet-shaped to aid insertion. Bore 74 may be dimensioned to receive a suture (not shown) so it can be pulled through the lumen if desired. Middle portion 70 is between proximal end portion 66 and distal end portion 68. Proximal end portion 66 includes a plurality of protrusions 76 adapted to frictionally retain proximal end portion 66 of fitting 62 within open end 12b of flexible tube 12.

In operation, a surgeon employs anvil delivery system 10 to position anvil assembly 16 in the body during minimally invasive procedures. During such procedures, the surgeon initially secures adaptor 14 to open end 12a of flexible tube, 12 and sutures anvil assembly 16 to central hub portion 14c of adapter 14. Flexible tube 12 may then be cut at any desired length. The cut creates a distal open end 12b from the blunt closed end in flexible tube 12. After cutting flexible tube 12, the surgeon secures fitting 62 in open end 12b. Specifically, proximal end portion 66 of fitting 62 is inserted into open end 12b. The frictional contact between protrusions 76 of distal end portion 66 of fitting 62 and the inner surface of flexible tube 12 secures fitting 62 to flexible tube 12.

For transoral applications, once fitting 62 has been secured to flexible tube 12, the surgeon inserts fitting 62 in the patent's mouth and moves fitting 62 along with flexible tube 12 down through the esophagus to the surgical site, e.g., stomach. It is also contemplated that the anvil delivery system can be used for other applications besides transoral insertion, such as transgastric and transanal approaches for colorectal, bariatric and other applications. This can be achieved due to the bullet shaped tip which can penetrate tissue, e.g. the stomach wall to deliver the anvil assembly. Other penetrating tip configurations could be provided.

After insertion, the surgeon should then make a small incision at the surgical site to create an inner access to the fitting 62. After making the incision, the surgeon pulls fitting 62 through the incision, thereby pulling anvil assembly 16 through the esophagus (or other body tissue or organ depending on the procedure) to the surgical site. If a suture is used through bore 74, the suture can be grasped and pulled to pull the anvil assembly. As flexible tube 12 is pulled through the incision, the distal end of center rod 20 of anvil assembly 16 advances through the incision. When anvil assembly 16 is properly positioned at the surgical site, the surgeon may release adapter 14 from anvil assembly 16 by cutting suture 40 and sliding center rod 20 from end 14b of adapter 14. Next, the flexible tube 12 (with fitting 62) and adapter 14 may be pulled from the body through the incision. The surgeon can now mount center rod 20 of anvil assembly 16 on a surgical stapling device (not shown) and perform the desired surgical procedure.

The components of anvil delivery system 10 may be provided in kit form. The kit may include a flexible tube 12 adapted to be secured to the anvil assembly 16, an adapter 14 configured to secure an anvil assembly 16 to the flexible tube 12 and a fitting 62 configured to be attached to flexible tube 12. Fitting 62, in turn, may include a body 64 having a proximal end portion 66 and a distal end portion 68, a blunt tip 72 disposed on the distal end portion 68, and a plurality of protrusions 76 disposed on the proximal end portion 66. Proximal end portion 66 of body 64 may be dimensioned to be supported within flexible tube 12. The plurality of protrusions 76 may be adapted to operatively attach the body 64 of the fitting 62 to flexible tube 12. Blunt tip 72 may be configured for insertion into a body lumen. Fitting 62 may include a bore 74 extending through distal end portion 68 of body 64. The kit may further include an anvil assembly 16. In one embodiment, the anvil assembly 16, the flexible tube 12, and adapter 14 are fastened together with a suture 50, as discussed above, and the fitting 62 is provided to blunt the end of flexible tube 12 if the flexible tube 12 has to be cut and to provide an insertion tip.

Figure 10A:
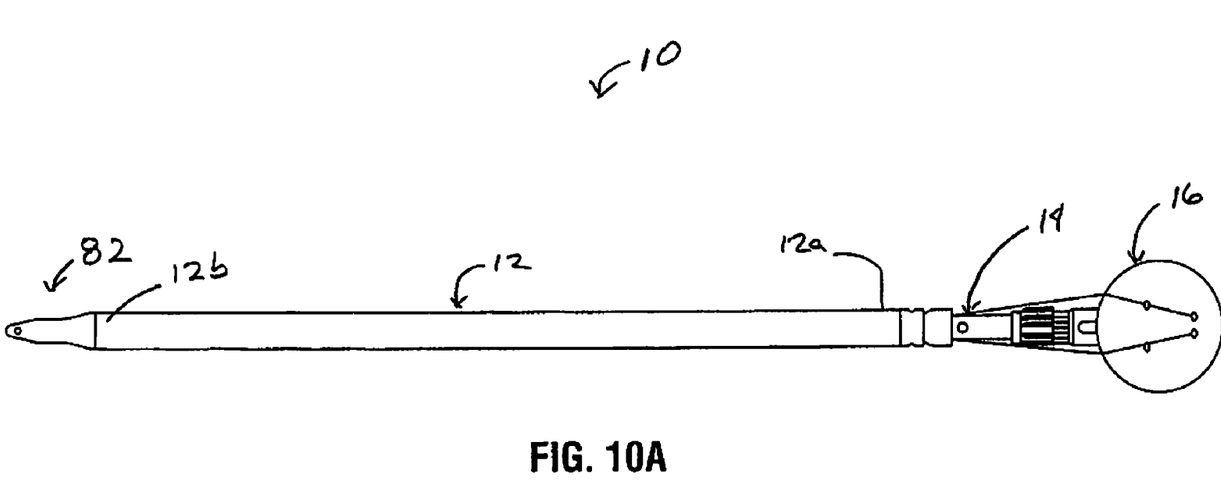
FIG. 10A is a top plan view of an anvil delivery system according to another embodiment of the present disclosure.
Figure 10B:
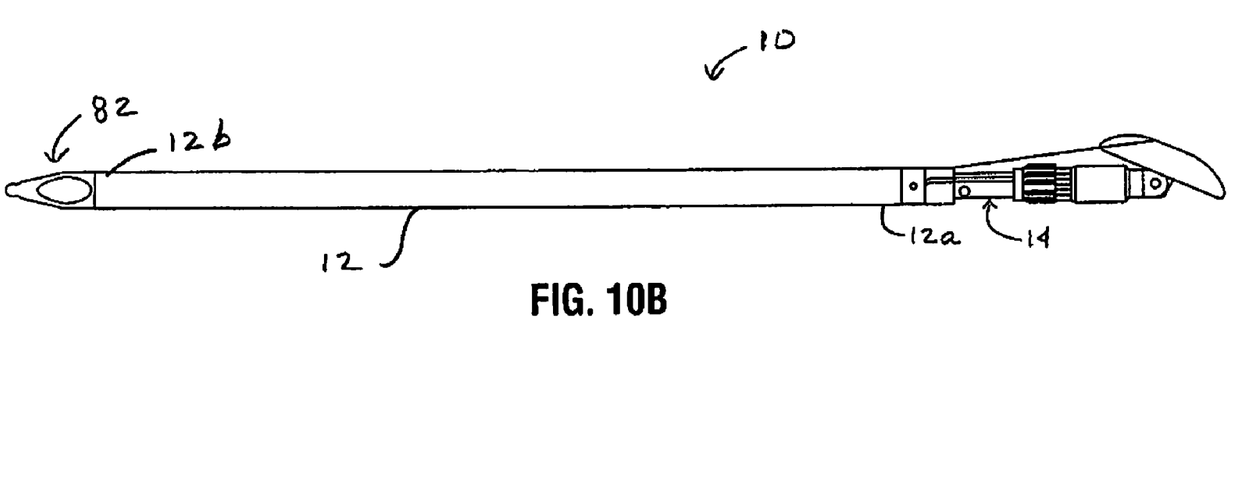
FIG. 10B is a side plan view of the anvil delivery system with the fitting shown in FIG. 10A.
Figure 11:
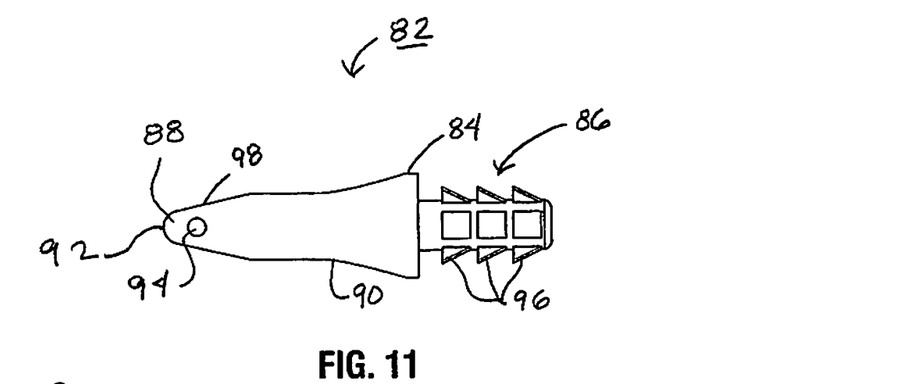
FIG. 11 is a top plan view of the fitting according to the embodiment of FIG. 10A.
Figure 12:
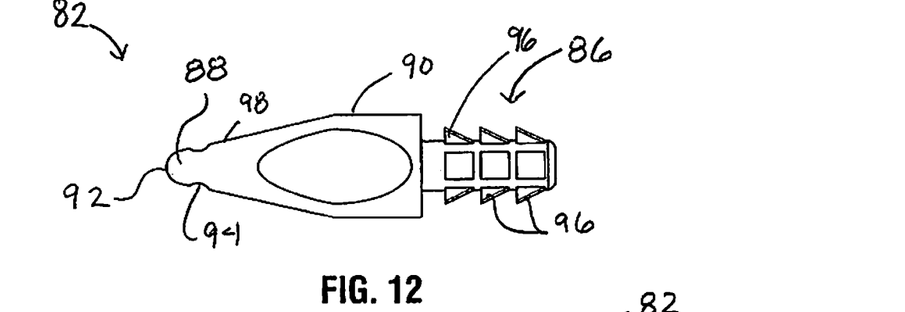
FIG. 12 is a side plan view of the fitting shown in FIG. 11.
Figure 13:
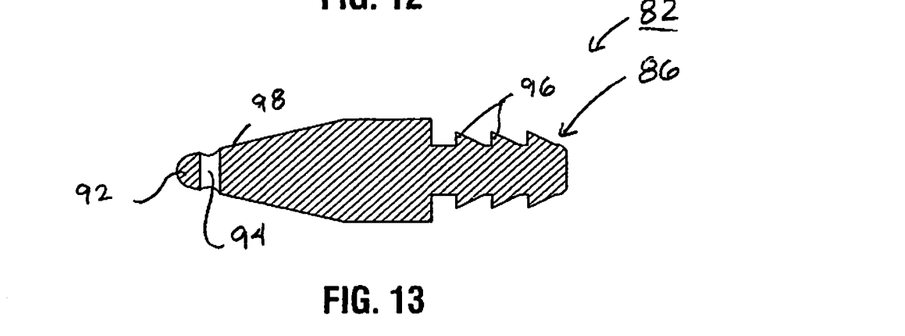
FIG. 13 is a cross-sectional side view of the fitting shown in FIG. 11.
Figure 14:
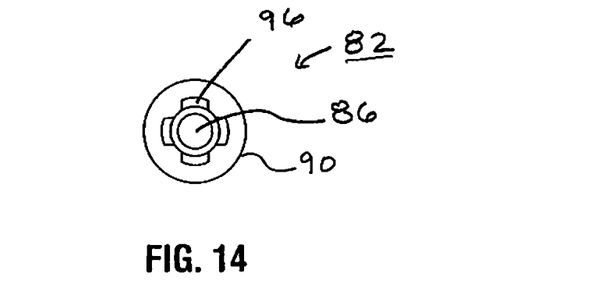
FIG. 14 is a rear plan view of the fitting shown in FIG. 11.

With reference to FIGS. 10A and 10B, another embodiment of anvil delivery system 10 includes an alternative fitting 82. Like fitting 62, fitting 82 is attached to open end 12b of tube 12 to facilitate smooth atraumatic passage of tube 12 through or into a body lumen. Since the structure and operation of an anvil delivery system 10 with fitting 62 is substantially identical to the structure and operation of an anvil delivery system 10 with fitting 82, the present disclosure only discusses in detail the structural features of fitting 82.

Referring to FIGS. 11-14, fitting 82 includes a body 84 having a proximal end portion 86 supported in open end 12b of flexible tube 12, a distal end portion 88, and a middle portion 90. Distal end portion 88 has a bore 94 defined therethrough and a blunt tip 92 configured for insertion into a body lumen such as the esophagus. Body 90 of fitting 82 has a tapered surface 98 leading to blunt tip 92. Tip 92 is bullet-shaped to aid insertion. Bore 94 is dimensioned to receive a suture (not shown). The suture is attached to tip 92 and pulled to pull tube 12 through a lumen if desired. Proximal end portion 86 includes a plurality of protrusions 96 adapted to frictionally retain proximal end portion 86 of fitting 82 within open end 12b of flexible tube 12. Protrusions 96 are disposed around an outer periphery of proximal end portion 86.

It will be understood that various modifications may be made to the embodiments disclosed herein. For example, the particular configuration of fitting 62 need not be exactly as shown but rather may be configured in any manner capable of facilitating atraumatic passage of tube 12 through a body lumen. Therefore, the above description should not be construed as limiting, but merely as exemplifications of the embodiments. Those skilled in the art will envision other modifications within the scope and spirit of the claims appended hereto.

The invention claimed is:

1. A method of performing a surgical procedure comprising:
    providing an anvil assembly having an anvil head and a flexible tube having a first end portion connected to the anvil assembly;
    providing a fitting having an insertion tip, the fitting being separate from the flexible tube;
    cutting a second end portion of the flexible tube, the second end portion being disposed on an opposite end of the tube from the first end portion;
    attaching the fitting to the cut second end portion of the flexible tube;
    inserting the insertion tip into tissue and advancing the insertion tip along with the flexible tube and anvil assembly to a desired site within a patient's body;
    removing the flexible tube from the anvil assembly and from the desired site leaving the anvil assembly in the patient's body at the desired site.

2. The method of claim 1, wherein the step of providing a fitting includes providing a fitting having a bore which receives a suture and the step of inserting the insertion tip includes the step of grasping the suture to pull the insertion tip to advance the fitting, flexible tube and anvil assembly within the patient's body to the desired site.

3. The method of claim 1, further including the step of securing the anvil assembly to the first end portion of the flexible tube using an adapter.

4. The method of claim 3, wherein the step of securing further includes the step of securing the anvil assembly to the adapter using a suture.

5. The method of claim 4, wherein the step of securing further includes inserting a first end of the adapter within the first end portion of the flexible tube to frictionally retain the adapter within the first end portion of the flexible tube.

6. The method of claim 4, wherein the step of removing the flexible tube from the anvil assembly includes cutting the suture to separate the anvil assembly from the adapter.

7. The method of claim 1, wherein the step of inserting the insertion tip into tissue includes inserting the insertion tip into a patient's mouth and advancing the insertion tip into the patient's stomach.

8. The method of claim 7, wherein the step of removing the flexible tube includes the step of making an incision at the desired site and pulling the fitting and the flexible tube through the incision.

9. The method of claim 8, wherein the step of pulling the fitting includes the step of pulling a suture extending through a bore in the fitting.

10. The method of claim 7, wherein the step of removing the flexible tube includes the step of making an incision at the desired site and pulling the fitting and the flexible tube through the incision.

11. The method of claim 1, wherein the step of inserting the insertion tip includes pulling the insertion tip through a lumen by pulling a suture extending through a bore in the insertion tip.

12. The method of claim 1, wherein the step of inserting the insertion tip includes inserting a penetrating tip of the insertion tip to penetrate tissue.

13. The method of claim 12, wherein the step of inserting the insertion tip into tissue includes inserting the insertion tip into a patient's mouth and advancing the insertion tip into the patient's stomach.

14. A method of performing a surgical procedure comprising:
- providing an anvil assembly having an anvil head and a flexible tube having a first end portion connected to the anvil assembly;
- providing a fitting having an insertion tip, the fitting being separate from the flexible tube;
- cutting a second end portion of the flexible tube, the second end portion being disposed on an opposite end of the tube from the first end portion;
- attaching the fitting to the second end portion of the flexible tube;
- inserting the insertion tip into tissue and advancing the insertion tip along with the flexible tube and anvil assembly to a desired site within a patient's body; and
- removing the flexible tube from the anvil assembly and from the desired site leaving the anvil assembly in a patient's body at the desired site;
- wherein the step of attaching the fitting includes the step of inserting a portion of the fitting within the second end portion of the flexible tube to frictionally engage the tube after the step of cutting has been completed.

15. A method of performing a surgical procedure comprising:
- providing an anvil assembly having an anvil head and a flexible tube having a first end portion connected to the anvil assembly;
- providing a fitting having an insertion tip, the fitting being separate from the flexible tube;
- cutting a second end portion of the flexible tube, the second end portion being disposed on an opposite end of the tube from the first end portion;
- attaching the fitting to the second end portion of the flexible tube;
- inserting the insertion tip into tissue and advancing the insertion tip along with the flexible tube and anvil assembly to a desired site within a patient's body; and
- removing the flexible tube from the anvil assembly and from the desired site leaving the anvil assembly in a patient's body at the desired site;
- wherein the step of providing a fitting includes providing a fitting having a bore which receives a suture and the step of inserting the insertion tip includes the step of grasping the suture to pull the insertion tip to advance the fitting, flexible tube and anvil assembly within the patient's body to the desired site; and
- wherein the step of attaching the fitting includes the step of inserting a portion of the fitting within the second end portion of the flexible tube to frictionally engage the tube after the step of cutting has been completed.

\* \* \* \* \*